United States Patent
Hahn et al.

(10) Patent No.: US 10,792,505 B2
(45) Date of Patent: Oct. 6, 2020

(54) LOW ENERGY CONVERSION OF VENTRICULAR TACHYCARDIA IN A SUBCUTANEOUS DEFIBRILLATOR

(71) Applicant: CARDIAC PACEMAKERS, INC., St. Paul, MN (US)

(72) Inventors: Stephen J. Hahn, Shoreview, MN (US); Paul Freer, Anaheim, CA (US); Venugopal Allavatam, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 440 days.

(21) Appl. No.: 15/232,191

(22) Filed: Aug. 9, 2016

(65) Prior Publication Data

US 2017/0050037 A1 Feb. 23, 2017

Related U.S. Application Data

(60) Provisional application No. 62/206,026, filed on Aug. 17, 2015.

(51) Int. Cl.
*A61N 1/362* (2006.01)
*A61N 1/39* (2006.01)
*A61N 1/05* (2006.01)

(52) U.S. Cl.
CPC ......... *A61N 1/3987* (2013.01); *A61N 1/0504* (2013.01); *A61N 1/3621* (2013.01); *A61N 1/3956* (2013.01)

(58) Field of Classification Search
CPC .. A61N 1/0504; A61N 1/3621; A61N 1/3756; A61N 1/3956; A61N 1/3987
See application file for complete search history.

(56) References Cited

U.S. PATENT DOCUMENTS

| | | |
|---|---|---|
| 5,366,487 A | 11/1994 | Adams et al. |
| 7,751,887 B1 | 7/2010 | Kroll et al. |

(Continued)

FOREIGN PATENT DOCUMENTS

| | | |
|---|---|---|
| EP | 0560569 A2 | 9/1993 |
| WO | 9319809 A1 | 10/1993 |
| WO | 2012170868 A1 | 12/2012 |

OTHER PUBLICATIONS

Janardhan et al., "A Novel Low-Energy Electrotherapy that Terminates Ventricular Tachycardia with Lower Energy than a Biphasic Shock with Antitachycardia Pacing Fails," Journal of the American College of Cardiology, vol. 60(23), pp. 2393-2398, 2012.

(Continued)

*Primary Examiner* — Allen Porter
(74) *Attorney, Agent, or Firm* — Seager, Tufte & Wickhem LLP

(57) ABSTRACT

Methods and devices for cardiac therapy. One example provides a subcutaneous anti-tachycardia pacing therapy. Another example provides a subcutaneous low energy cardioversion therapy. Yet another example provides a subcutaneous multiple pulse cardioversion therapy. In various examples, specific steps are taken to ensure synchronization of delivered therapy when provided in response to sensing and analysis of a subcutaneous signal. Some examples use a substernal device instead.

18 Claims, 13 Drawing Sheets

(56) References Cited

U.S. PATENT DOCUMENTS

| | | | |
|---|---|---|---|
| 8,116,867 B2 * | 2/2012 | Ostroff | A61N 1/3621 |
| | | | 600/515 |
| 8,483,841 B2 | 7/2013 | Sanghera et al. | |
| 8,509,889 B2 | 8/2013 | Efimov et al. | |
| 8,565,878 B2 | 10/2013 | Allavatam et al. | |
| 2002/0091414 A1 | 7/2002 | Bardy et al. | |
| 2012/0029335 A1 | 2/2012 | Sudam et al. | |
| 2012/0215269 A1 | 8/2012 | Tandri et al. | |
| 2012/0316613 A1 | 12/2012 | Keefe et al. | |
| 2014/0330325 A1 | 11/2014 | Thompson-Nauman et al. | |

OTHER PUBLICATIONS

Ratner et al., "Terminating ventricular tachyarrhythmias using far-field low-voltage stimuli: Mechanisms and delivery protocols," Heart Rhythm, vol. 10(8), pp. 1209-1217, Aug. 2013.
"International Application Serial No. PCT/US2012/041633, International Search Report dated Aug. 24, 2012," 3 pgs.
"International Application Serial No. PCT/US2012/041633, Written Opinion dated Aug. 24, 2012," 6 pgs.

* cited by examiner

LOW ENERGY CONVERSION OF VENTRICULAR TACHYCARDIA IN A SUBCUTANEOUS DEFIBRILLATOR

CROSS REFERENCE TO RELATED APPLICATIONS

The present application claims the benefit of and priority to U.S. Provisional Application Ser. No. 62/206,026, filed on Aug. 17, 2015 and titled LOW ENERGY CONVERSION OF VENTRICULAR TACHYCARDIA IN A SUBCUTANEOUS DEFIBRILLATOR, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

An illustration is provided in FIG. 1. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

In its original implementation, the S-ICD System™ provides two therapy outputs: high energy defibrillation, and a temporary pacing output for treating post-defibrillation bradycardia or asystole. The pre-market approval notice for the S-ICD System™ in the United States excludes from the indications for use those patients having spontaneous, frequently recurring ventricular tachycardia (VT) that is reliably terminated with anti-tachycardia pacing (ATP).

For preservation of battery life and enhanced patient comfort, it is desirable to make a low energy conversion regimen for VT available in such systems. Certain prior references have discussed providing ATP from a subcutaneous defibrillation system, however, additional alternatives are desired and further details for delivery, for example, of ATP are also desirable. In addition, therapy options that may expand the indications for use of systems similar to the S-ICD System™ are desired.

SUMMARY

A problem to be solved is the desire for additional approaches to the treatment of ventricular tachycardia in a subcutaneous cardiac therapy device. One example provides a subcutaneous anti-tachycardia pacing therapy. Another example provides a subcutaneous low energy cardioversion therapy. Yet another example provides a subcutaneous multiple pulse cardioversion therapy. In some examples, specific steps are taken to ensure synchronization of delivered therapy relative to the cardiac cycle.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
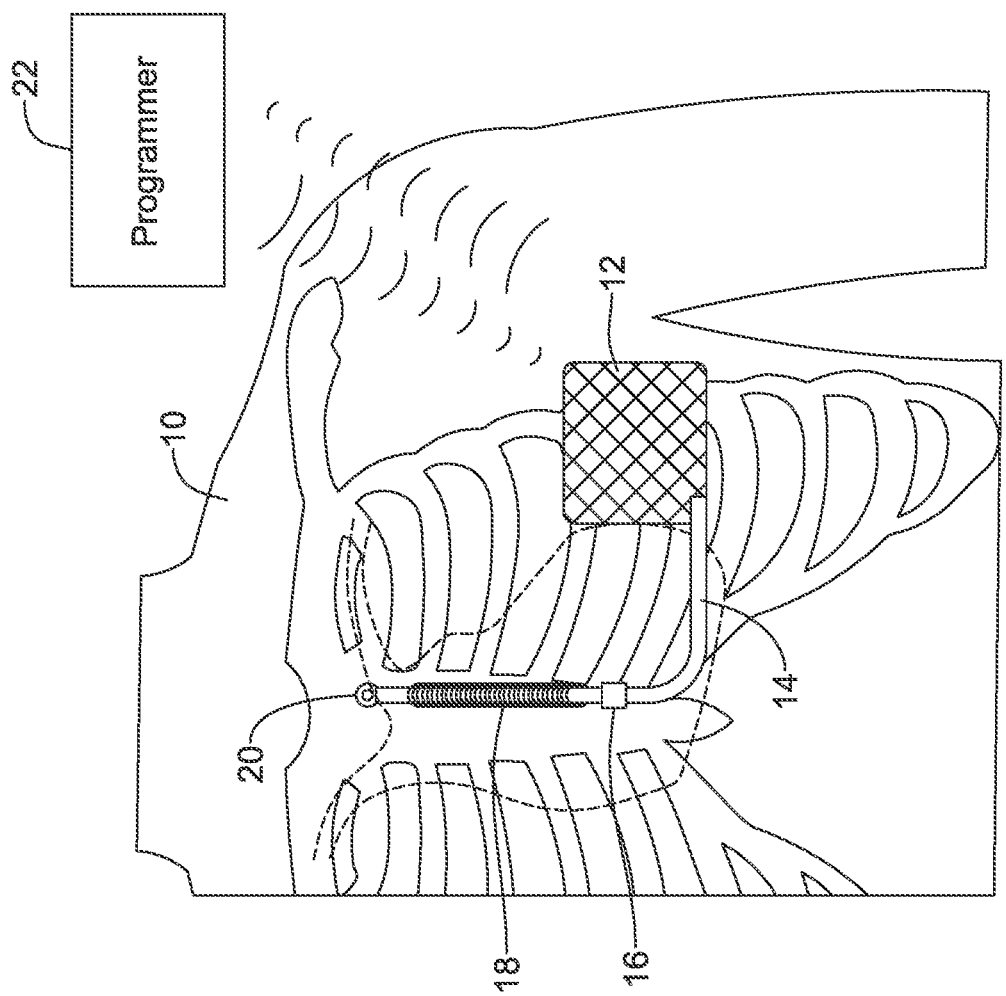
FIG. 1 shows an illustrative subcutaneous-only implantable cardiac stimulus system in an implanted state.

FIG. 1 shows an illustrative subcutaneous-only implantable cardiac stimulus system in an implanted state. It should be noted that other implant positions may be used instead for a subcutaneous-only system, such as a system with a lead or canister on the right side, or with one of the lead or canister anterior on the chest and the other posterior on the back of the patient. In some examples, one or more transvenous or epicardial leads may be provided to serve one or more purposes such as sensing and/or therapy delivery. The implantable system may be configured to operate cooperatively or in parallel with additional implantable devices such as a cardiac monitor, pacemaker, ventricular assist device or pump, defibrillator, leadless pacemaker, cardiac resynchronization system, pump for drugs or other substances, neural stimulator, etc.

In one example, a substernal system may be provided rather than a subcutaneous-only system. For example, a substernal system may be emplaced as described in U.S. Patent Application No. 62/195,695, or US PG Publication 20140330325, for example, and the disclosures of both of which are incorporated herein by reference. Such a system may substitute a substernally placed lead for lead 14 shown in FIG. 1, or may include a substernally placed lead in addition to lead 14. A substernal lead is to be implanted without entering or touching the heart and may be referred to as extravascular. Throughout the following discussion, any example of a subcutaneous defibrillator should be understood as applying as well to a substernal system. Any discussion of a therapy delivered, or a signal sensed, between two subcutaneously located electrodes may instead be delivered using a first electrode on a subcutaneous device (lead or canister) and a second electrode on a substernal lead, or between two electrodes disposed on a substernal lead.

The canister 12 contains operational circuitry for the implantable system. The operational circuitry may include a controller and any suitable analog and/or digital circuits needed for signal processing, memory storage and generation of high-power electrical, low-power electrical and/or non-electrical outputs. The operational circuitry may include suitable battery technology for an implantable device, with any of numerous examples well known in the art, and may use various capacitor technologies to assist in the short term build-up and/or storage of energy for defibrillation or other high output purposes.

The lead 14 and external shell for the canister 12 can be manufactured with various materials suitable for implantation, along with coatings for such materials, well known in the art. For example, the canister 12 can be made using titanium, with a titanium nitride or iridium oxide (or other material) coating if desired, and the lead 14 can be formed with a biocompatible material such as a polyether, polyester, polyamide, polyurethane, polycarbonate, silicon rubber and blends or copolymers thereof. The electrodes 16, 18, 20 can be formed of suitable biocompatible materials such as silver, gold, titanium or stainless steel such as MP35N stainless steel alloy, or other materials. For example, a lead may be designed as shown in any of U.S. Pat. No. 8,483,841, US PG Pub. No. 20120029335, and/or U.S. Provisional Patent Applications 62/344,042 and 62/331,721, the disclosures of each of which are incorporated herein by reference.

In some examples, the system may include one or more sensors to detect signals in addition to the cardiac electrical signal that can be captured using selected combinations of the electrodes 16, 18, 20 and canister 12 shown in FIG. 1. Such additional sensors may include, for example, temperature sensors, accelerometers, microphones, optical sensors and chemical sensors, among others. The programmer 22 and implantable device 12 may communicate with one another using, for example and without limitation, inductive or RF telemetry, or any other suitable communication solution. The present invention may be embodied in a system having any such characteristics.

Figure 2:
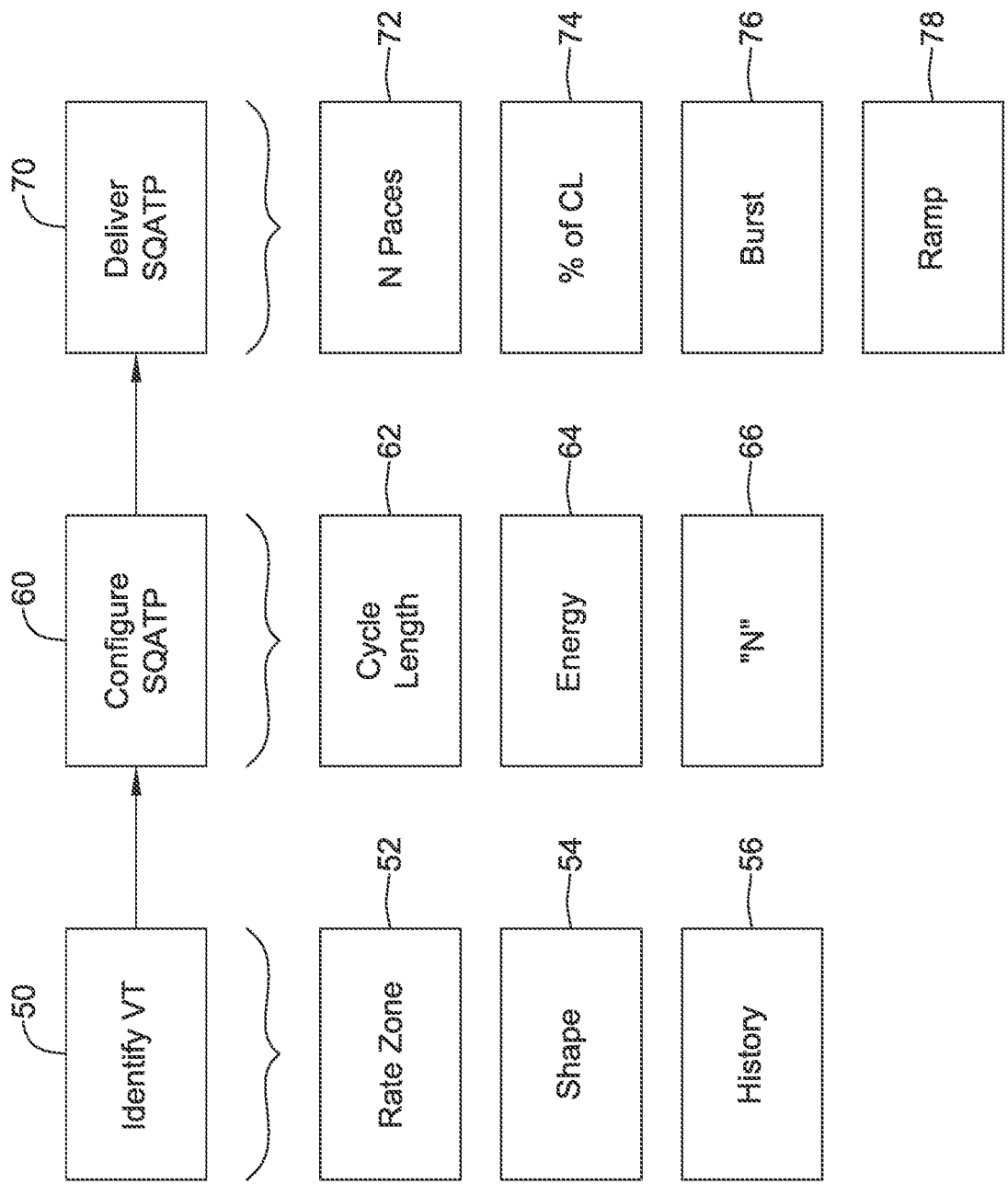
FIG. 2 is a block flow diagram for a subcutaneous anti-tachycardia pacing therapy.

FIG. 2 is a block flow diagram for a subcutaneous anti-tachycardia pacing therapy. The method comprises identifying a ventricular tachycardia 50, configuring a subcutaneous anti-tachycardia pacing (ATP) therapy 60, and delivering the configured ATP therapy 70. The step of identifying a ventricular tachycardia 50 may comprise consideration of detected rate 52, for example, whether the rate falls within a predefined zone suitable for ATP therapy rather than defibrillation therapy (typically higher rates) or no therapy (lower rates). For example, a rate zone may be adjustable within a range of about 180-240 beats per minute (bpm), or lower or higher, as desired. In some examples the rate zone 52 may extend down to rates as low as 120 bpm. Rate may be determined for purposes of block 52 using any suitable method, such as by detecting cardiac cycles using, for example, R-waves, heart sounds, or blood pressure changes, and establishing a rate therefrom, and/or by the use of the methods and devices for self-correlation to obtain rate, as disclosed in U.S. patent application Ser. Nos. 14/819,817, 14/819,851, and 14/819,889, the disclosures of which are incorporated herein by reference.

The signal shape or morphology may be considered as noted at 54. For example, it is believed that the type of tachycardia well suited to therapy with ATP will exhibit a monomorphic shape—that is, a repeatable and consistent shape of the electrical cardiac waveform, whether captured as a cardiac electrogram (EGM) from within the heart or as a subcutaneous electrocardiograph (ECG). A polymorphic tachycardia, in contrast, would typically be treated using higher power defibrillation. The distinction between monomorphic and polymorphic signals may be determined by comparing the cardiac signal—often the R-wave or combination of Q, R and S waves or QRS complex—to a stored or dynamic template, or even comparing one detected beat to another close-in-time beat. Wavelet, principal components, and correlation waveform analyses are but a few of many different ways to compare signals to determine whether the signal is monomorphic or not.

Width may also be considered at 54. A cardiac signal having a narrow width and elevated rate can arise due to exercise induced elevated heart rate, for which therapy may be withheld, for example. However, a ventricular tachycardia characterized by an elevated rate and wide QRS signals or wide R-waves may be deemed treatable as likely a result of a ventricular originating arrhythmia such as a treatable ventricular tachycardia.

The patient's history 56 may also be considered when identifying the ventricular tachycardia 50. For example, if a previous ATP was delivered to the patient and succeeded in terminating a ventricular tachycardia, characteristics of the prior condition may be stored for later comparison to newly detected conditions. For example, a template may be stored for use in the shape comparison at 54 based on the prior event. Additionally, the rate zone 52 may be modified in light of patient history 56, to raise or lower rate boundaries in light of prior success or failure of ATP.

The configuration of a subcutaneous ATP 60 may include several considerations. For example, the cycle length 62 of the ventricular tachycardia identified at block 50 may be measured. Cycle length may be used to establish parameters of the subcutaneous ATP 60 to be delivered. For example, a coupling interval between the first delivered pulse forming the ATP therapy can be calculated as a percentage of the cycle length 62, in the event that the subcutaneous ATP is to be delivered synchronously. In another example, the interval (s) between delivered pulses forming the ATP may be calculated as percentage(s) of the cycle length 62.

The energy level 64 of the subcutaneous ATP may also be calculated. The energy level 64 may be controlled in terms of voltage or amplitude or delivered energy, depending on various factors of a given system. In some examples, energy levels 64 may be preset. In other examples, energy levels 64 may be modified based on whether previously delivered therapy was successful. Energy levels 64 may also be modified in light of observed patient conditions such as, for example, detected impedance across the patient's thorax. For example, if observed impedance is relatively higher, then a higher power or energy level 64 may be configured.

The number of pulses to include in ATP, "N" 66, may be calculated as well. For example, in a system that tracks the success or failure of prior therapy delivery, "N" may be set by reference to a prior successful therapy (by selecting the same "N" as the prior therapy), or by reference to a prior failed therapy (by setting "N" to be higher than the failed therapy), or by reference to a default in the event that a different therapy setting (such as higher energy) is being used relative to a prior failed or successful therapy. In some examples, on the other hand, "N" may be preset by a physician in a range of, for example, 2 to 20, or more.

In one example, if prior therapy was not successful, coupling intervals calculated from the cycle length 62 (whether for synchronization or interpulse delays) may be modified, the energy 64 may be increased or decreased, and the quantity of output pulses "N" 66 may be increased or decreased. The configuration step 64 may include preparing a therapy delivery capacitor by charging the therapy delivery capacitor to a desired level.

The subcutaneous ATP, once configured, can then be delivered. A quantity of pace outputs 72 is delivered, using a percentage of the cycle length 74 for synchronization and/or for interpulse delays. In some examples, a burst form 76 may be used, in which each pulse is delivered with the same interpulse delay, set as a fixed percentage of the cycle length of the underlying ventricular tachycardia. In other examples, a ramp form 78 may be used, in which the pulses delivered in ATP therapy are separated by a decrementing cycle length. That is, each subsequent pulse in the ATP therapy is separated from a preceding pulse by a smaller interval than the one before it.

Figure 3:
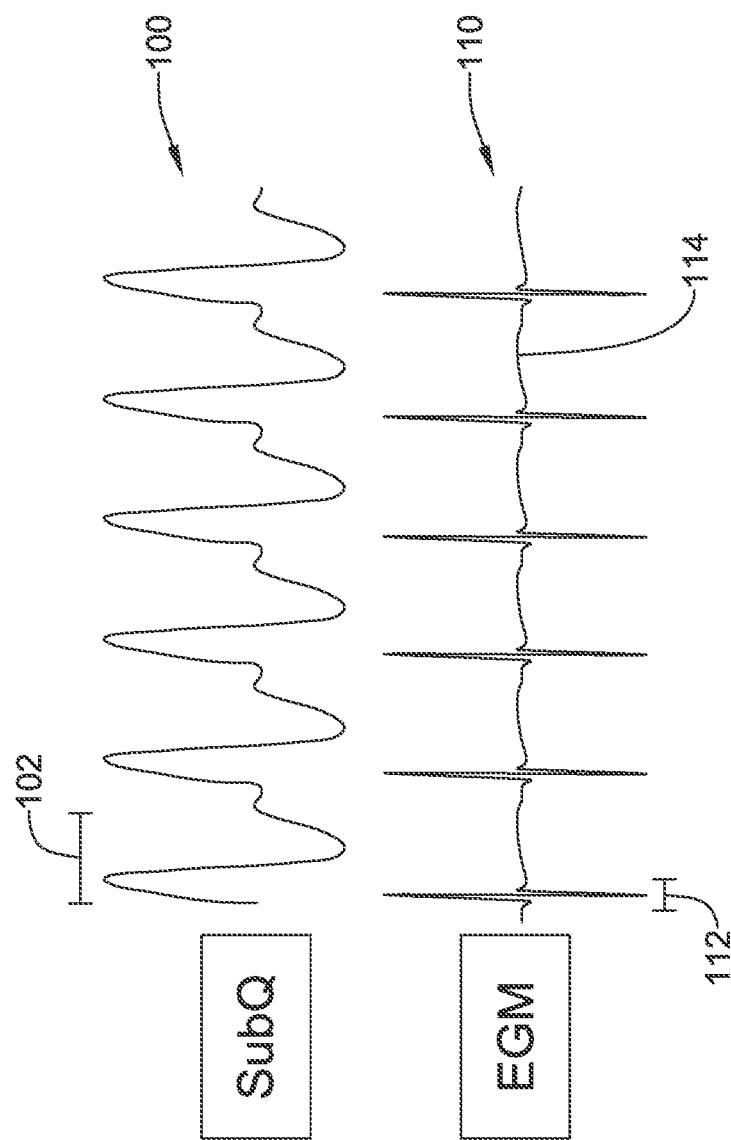
FIG. 3 compares a subcutaneously captured cardiac signal to a cardiac signal as detected with intracardiac electrodes.

There are various reasons why synchronization of ATP—or other therapy—may be a challenge in a subcutaneous-only system or when analysis is performed on a subcutaneously captured signal. For illustration, FIG. 3 compares a subcutaneously captured cardiac signal to a cardiac signal as detected with intracardiac electrodes. The subcutaneous ECG is shown at 100. An individual cardiac cycle as observed in the subcutaneous ECG has an R-wave width as shown at 102. The EGM signal captured using an intracardiac or epicardial electrode is shown at 110. The R-wave 102 in the subcutaneous ECG is much wider than the R-wave 112 in the intracardiac EGM. The QRS complex width of the subcutaneous ECG 100 is also wider, in like fashion, than that of the EGM 110. Moreover, often a treatable ventricular tachycardia would be characterized as having wide R-waves or QRS complexes.

In addition to the challenges presented by width, the baseline presents a challenge. In the EGM, as shown at 114, the signal is at baseline most of the time. However, particularly during some ventricular tachycardia episodes such as that shown in FIG. 3, the subcutaneous ECG 100, even when filtered to a range of about 3 to 40 Hz, spends little time at baseline.

Figure 4:
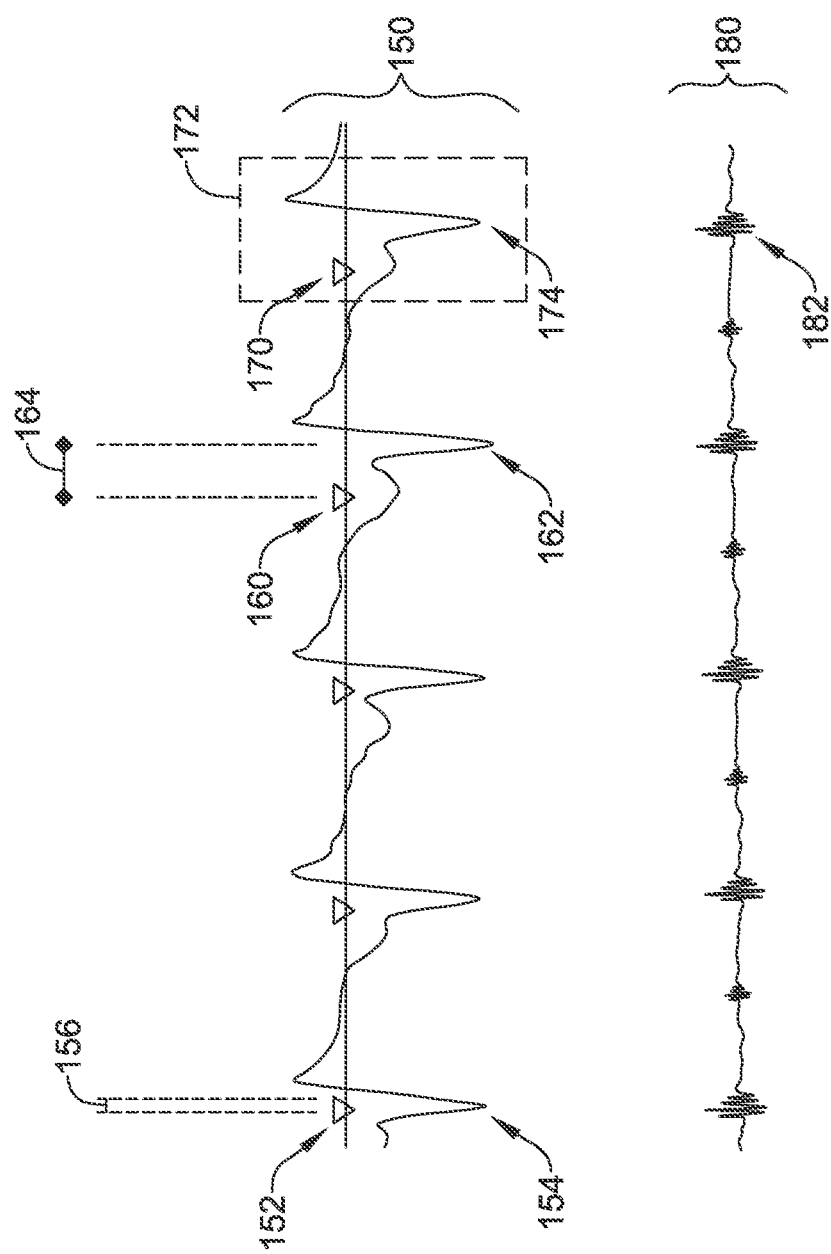
FIG. 4 illustrates certain detection and alignment issues that can arise when sensing a subcutaneous signal.
Figure 6:
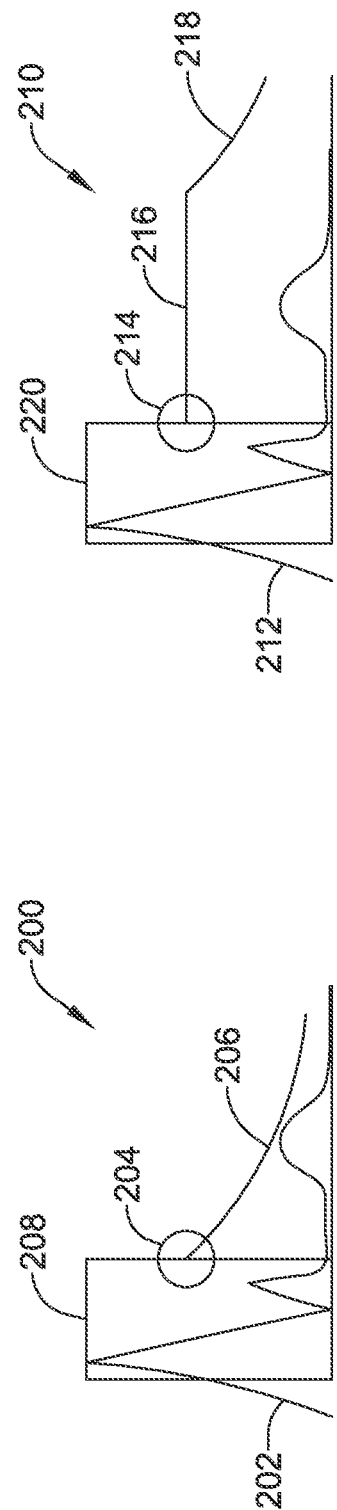
FIG. 6 compares a first detection profile with a second detection profile.

FIG. 4 further illustrates the challenges the subcutaneous signal presents. A subcutaneous ECG is shown at 150 for a ventricular tachycardia signal. An R-wave detection algorithm has been applied to the subcutaneous ECG 150, and individual detections are shown by the triangles such as 152, 160 and 170. (An illustrative R-wave detection profile is shown in FIG. 6). In some of the cardiac cycles shown in FIG. 4, the R-wave detection 152 is closely synchronized with the actual R-wave peak 154, as illustrated at 156. However, later, the R-wave detection 160 is separated from the actual R-wave peak 162, as highlighted at 164. Thus, relying simply on the R-wave detections 152, 160 will not yield consistent synchronization information.

FIG. 4 also shows two potential solutions for better synchronization information. In one example, a peak searching step is added. For example, when an R-wave detection is declared at 170, a peak search window 172 can be defined. The maximum peak within the window 172, shown here at 174, can be declared the actual R-wave peak. This may provide more consistent synchronization information.

In another example, heart sounds may be measured. Heart sounds may be identified by providing a microphone, such as a piezoelectric transducer, in the implantable device. Heart sounds may also be identified by the use of an accelerometer. Heart sounds may be obtained from a second implantable device if, for example, a subcutaneous cardiac stimulus device is used in conjunction with an intracardiac leadless pacemaker. For example, the second device may communicate a signal indicative of heart sounds, or may detected a heart beat using heart sounds and provide an output at the time of the beat.

Heart sounds are shown in FIG. 4 illustratively at 180, with the first and second heart sounds (as those terms are used by those skilled in the art) being shown. First heart sound 182 emanate from the closure of the atrioventricular valves, primarily, and is coincident with the peak of the R-wave. In an example, to ensure differentiation from the second heart sound, the R-wave detection 170 may be used to start a listening cycle to observe first heart sound 182. Heart sounds may be affected by electro-mechanical delay as the peak R-wave, in the electrogram, may not coincide with the resulting heart sound, and an accommodation for such delay may be made by, for example, measuring such a delay. The heart sounds are noted here in FIG. 4 for reference purposes; other embodiments may use other second signals, as noted further with respect to FIG. 5, below.

Figure 5:
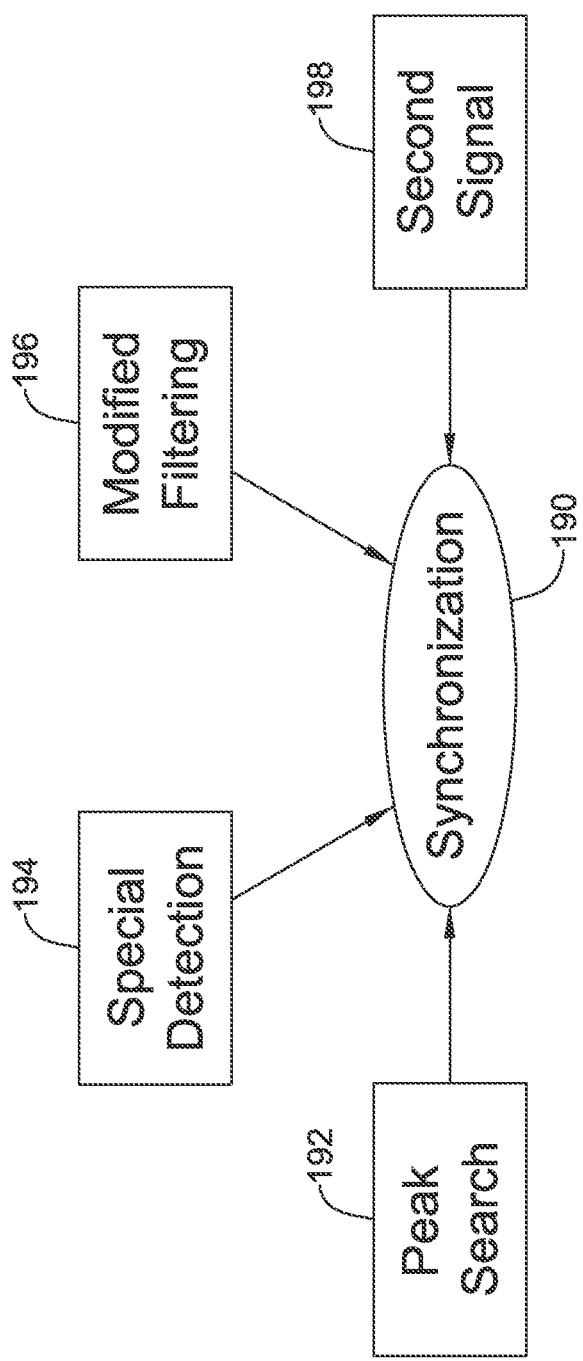
FIG. 5 identifies several alternatives for synchronization which may be used separately or in various combinations.

FIG. 5 illustrates several options for synchronization which may be used separately or in various combinations. Synchronization 190 may be achieved using one or more of the peak search 192 (174 in FIG. 4), a special detection profile 194 (FIG. 6), modified filtering 196, or a second signal 198 (180/182 in FIG. 4). In further examples, the modified filtering 196 may include, for example, applying additional filtering to the captured cardiac signal to flatten out the baseline or to remove, for example, non-synch information such as the T-wave or P-wave. In one example, ordinary detection may be performed using a bandwidth in the range of 3 Hz to 40 Hz, with modified filtering 196 for synchronization 190 adding an extra high pass filter in the range of 3-10 Hz, for example, at 8 or 9 Hz.

The use of a second signal 198 may include use of heart sounds, for example as shown in FIG. 4 above at 180/182. In other examples, a blood pressure monitor may be provided, or a motion sensor, to identify a cardiac output or muscle movement as a second signal 198. The second signal 198 may be sensed by the same device that delivers therapy, or it may be sensed by a second device and communicated from a second device disposed at a different location in or on the patient. Such communication may include a signal representative of a physiological second signal, or may simply be a marker or indicator that a predefined event has been sensed by the second device. For example, the second signal may be an intracardiac EGM sensed by a leadless intracardiac pacemaker and communicated to a subcutaneous-only defibrillator, or the second signal may be a marker generated by a leadless intracardiac pacemaker upon detecting an R-wave or QRS complex.

FIG. 6 compares a first detection profile with a second detection profile. A detection profile is a template used to define a detection threshold to be applied to an ECG or EGM, as the case may be, to detect cardiac cycles. In general detection profiles for ventricular detection may be intended to apply a threshold that will be crossed by the R-wave or QRS complex of each cardiac cycle. Some examples of detection profiles and uses therefore can be found in U.S. Pat. No. 8,565,878, the disclosure of which is incorporated herein by reference.

An example is shown at 200. The subcutaneous ECG is shown at 202. A detection threshold defined by the profile starts at a first level 204 and undergoes an exponential decay as shown at 206 toward a noise floor. The level set at 204 may be set by reference to the peak height of the R-wave or maximum peak of the QRS complex and setting the level at 204 to a percentage (30% to 70%, or higher or lower, for example).

To avoid detecting the same cardiac cycle twice, a refractory period 208 is applied for a period encompassing the QRS complex, as shown. During the refractory period 208, additional cardiac cycle detections are not allowed to occur. Once the refractory period 208 expires, a crossing of the detection threshold 206 can be declared as a new cardiac cycle, subject to analysis for noise and overdetection, for example, for which numerous examples may be found in various patents cited below.

The present inventors have determined that the application of the exponential decay at 206 can increase the likelihood of inconsistent alignment of the R-wave "detection" to the actual R-wave peak, as illustrated in FIG. 4, by, for example, allowing detection threshold crossing by the P-wave, or other artifact, or by a subcutaneous ECG which fails to reside at baseline. Thus in one example, rather than the profile shown at 200, a "Synch" profile may be applied as shown at 210.

The "Synch" profile 210 is shown relative to the subcutaneous ECG 212. The beginning point of the detection threshold is shown at 214, however, rather than going directly to an exponential decay 218, a constant threshold period 216 is applied first. The combined duration of the refractory period 220 and constant threshold period 216 may be, for example, in the range of 350 to 450 milliseconds, though longer or shorter combined durations may be used. For example, a combined duration of 400 milliseconds would mean that if the cardiac rate is over 150 bpm, a new R-wave should occur prior to expiration of the constant threshold period 216 since the expected interval between R-waves would be less than 400 milliseconds. Because it uses higher thresholds than profile 200, the "Synch" profile 210 may be reserved for use when preparing to deliver a synchronized therapy such as a synchronized subcutaneous ATP (or a low energy cardioversion as in FIGS. 9-10, below) to avoid undersensing if the underlying cardiac rhythm degrades into a low amplitude ventricular fibrillation.

Figure 7:
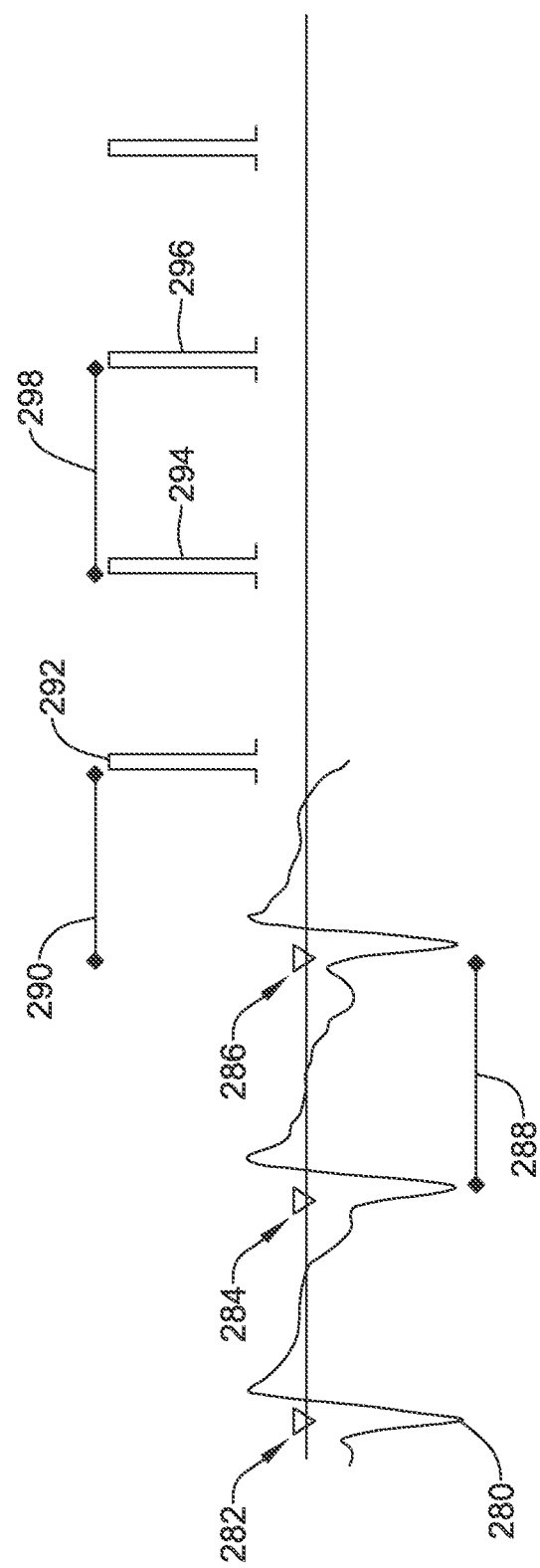
FIG. 7 is a graphic illustration of the delivery of a subcutaneous anti-tachycardia pacing therapy.

FIG. 7 is a graphic illustration of the delivery of a subcutaneous anti-tachycardia pacing therapy. The subcutaneous ECG is shown at 280, with R-wave detections at 282, 284, and 286. These R-wave detections 282, 284, 286 can be used to determine the average cycle length (1 to 4, or more, R-R intervals can be used, for example), shown at 288. For a synchronized waveform, a first ATP pulse coupling interval 290 can be set based on the average cycle length 288. Alternatively, the interval at 290 may be predetermined or fixed, or a percentage of the average cycle length 288.

Next a series of pulses are applied, as shown at 292, 294, 296. For a burst therapy regimen, the interpulse coupling interval 298 may be fixed—that is, the same interval separates pulse 292 from pulse 294 and pulse 294 from pulse 296. For a ramp therapy regimen, the intervals decrease with each additional pulse being delivered. In either burst or ramp therapy, the interval 298 is some percentage (less than 100%) of the average cycle length 288.

Figure 8:
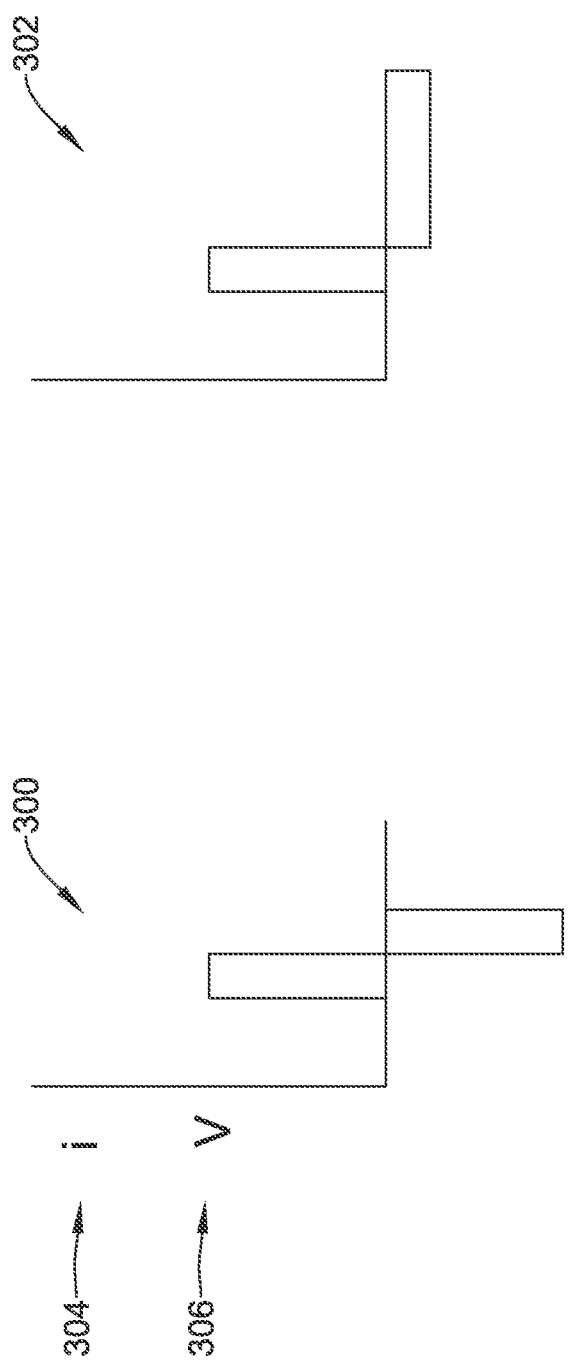
FIG. 8 shows certain illustrative waveforms for anti-tachycardia pacing.

For illustrative purposes and simplicity in the drawing, the delivered pulses 292, 294, 296 are shown as monophasic and constant in amplitude. FIG. 8 shows a couple of many alternatives for subcutaneous ATP. At 300, a biphasic therapy is shown, with a positive phase and a negative phase; the phases may be balanced or imbalanced in various embodiments. A monophasic pulse is shown at 302, with a passive recovery following the output pulse. Outputs may be controlled by current, as indicated at 304, or by voltage, as shown at 306. Some examples include constant or decaying current or voltage waveforms in monophasic, biphasic, or other multi-phasic waveforms.

Figure 9:
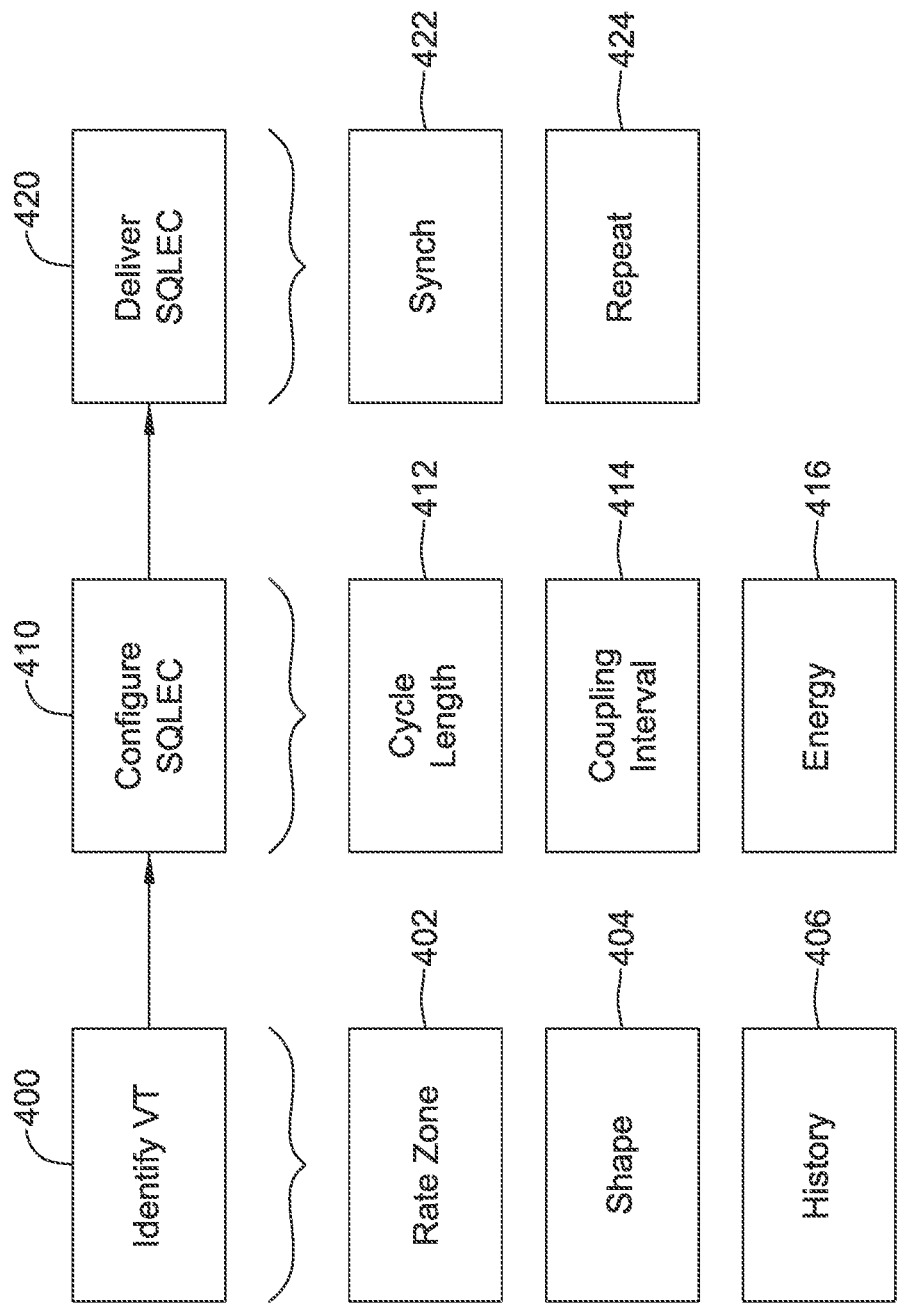
FIG. 9 is a block flow diagram for a subcutaneous low energy cardioversion therapy.

FIG. 9 is a block flow diagram for a subcutaneous low energy cardioversion therapy. At block 400, the ventricular tachycardia is identified. Next a subcutaneous (SQ) low energy cardioversion (LEC) therapy is configured at 410. Finally, the subcutaneous low energy cardioversion therapy is delivered at 420.

The identification of a ventricular tachycardia may be similar to that described above for FIG. 2, including for example the use of a rate zone 402, consideration of shape, morphology and/or width 404, and the patient or device history 406. Considerations of patient history may include, for example, recalling whether a VT was identified but not converted, either with an LEC therapy, in which case a different voltage, current, energy or waveform may be automatically applied, for example, or whether a non-LEC therapy (such as ATP or multiple-pulse conversion discussed below) was applied and failed.

Configuration of the subcutaneous low energy cardioversion 410 may include the measurement of an average cycle length for the ventricular tachycardia. From the cycle length, a coupling interval for the delivery of the subcutaneous low energy cardioversion therapy is calculated at 414. Again the coupling interval can be a percentage of the cycle length.

Finally an energy level is defined as noted at 416. The subcutaneous low energy therapy in some examples, provides a therapy output that is about one order of magnitude (or more) lower in terms of one or more of energy delivered, peak voltage, or peak current, than the defibrillation therapy of the subcutaneous device. For example, subcutaneous defibrillators as originally approved by the US Food and Drug Administration in PMA P110042 delivered a standard ambulatory defibrillation therapy of 80 Joules, with intraoperative testing at 65 Joules (though some physicians also tested at 55 Joules). The low energy cardioversion 416 in this instance would be in the range of about 0.5 Joules up to about 10 Joules in preferred embodiments of the low energy cardioversion, although higher or lower energy levels may be used instead.

Delivery of the subcutaneous low energy cardioversion therapy 420 may include synchronization 422. Synchronization may be accomplished by setting a delay interval after a most recent R-wave to ensure the low energy cardioversion therapy is not delivered on the T-wave (which may be pro-arrhythmic), and/or at an optimal time of the cardiac cycle. If a first delivered therapy does not succeed, one or more repeats 424 may be performed, with, for example, a higher energy 416, different shape, or other changes.

Figure 10:
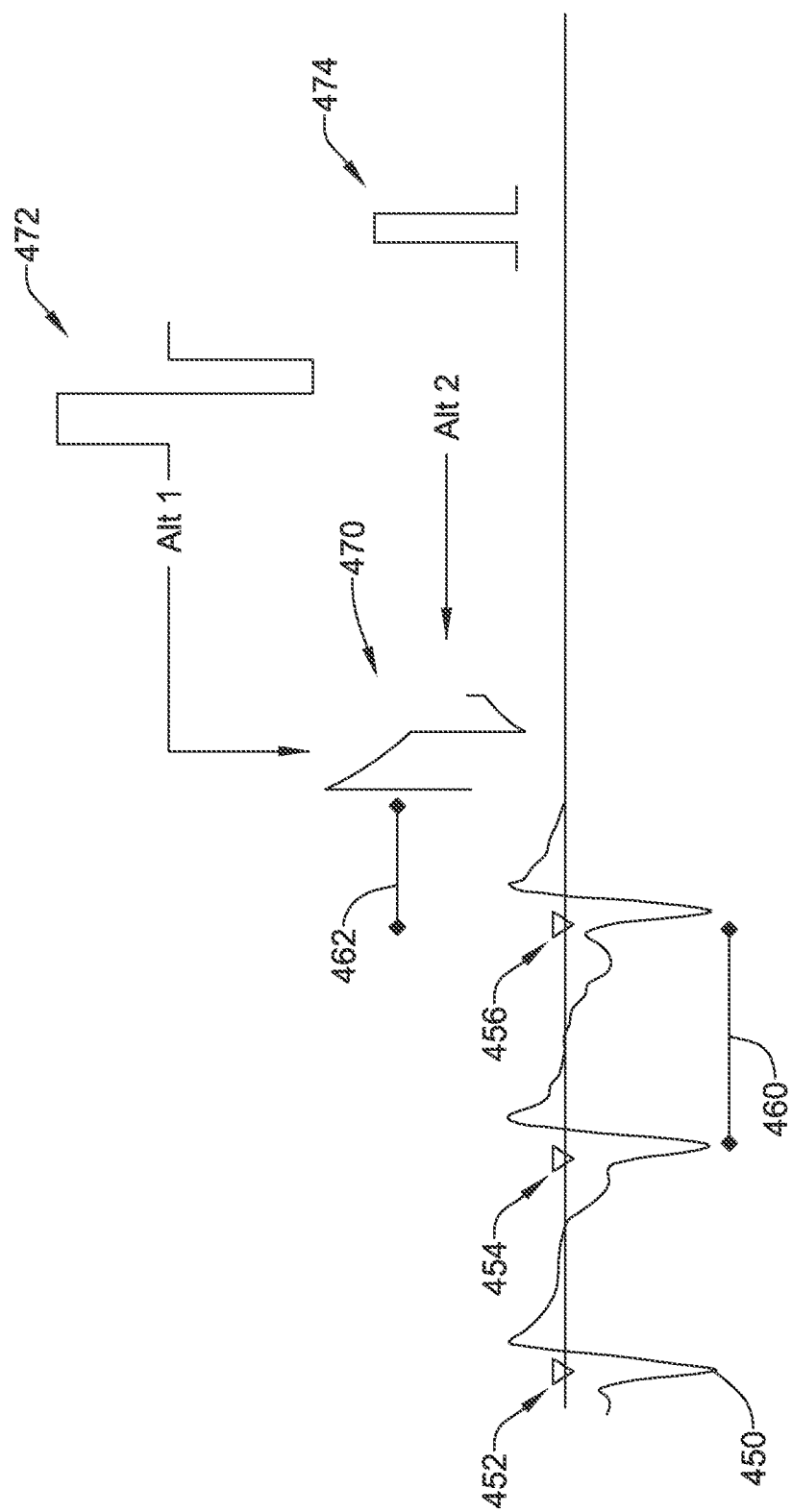
FIG. 10 is a graphic illustration of the delivery of a subcutaneous low energy cardioversion therapy.

FIG. 10 is a graphic illustration of the delivery of a subcutaneous low energy cardioversion therapy. The subcutaneous ECG is shown at 450, with R-wave detections occurring at 452, 454 and 456. A cycle length 460 of the ventricular tachycardia is calculated, and a therapy coupling interval 462 is calculated for the therapy delivery. The therapy coupling interval 462 may be some percentage (less than 100%-as low as 0%) of the cycle length 460. The therapy coupling interval, as noted above, may be selected to be at least long enough to avoid placing the low energy cardioversion therapy on the T-wave of the cardiac signal 450. The synchronization concepts illustrated in FIG. 5 may be used to trigger the start of the coupling interval 462.

The low energy cardioversion therapy 470 is shown as a biphasic truncated exponential, with phase imbalance so that the second phase is about 40% to about 80% of the duration of the first phase. In other examples the phases may be equal. Some alternatives are shown as well in FIG. 10. For example, a biphasic, constant voltage or constant current waveform may be used instead, as shown at 472. In another example, a constant current or constant voltage monophasic waveform may be used, as indicated at 474. If desired, triphasic or other multi-phasic therapy may be provided.

Figure 11:
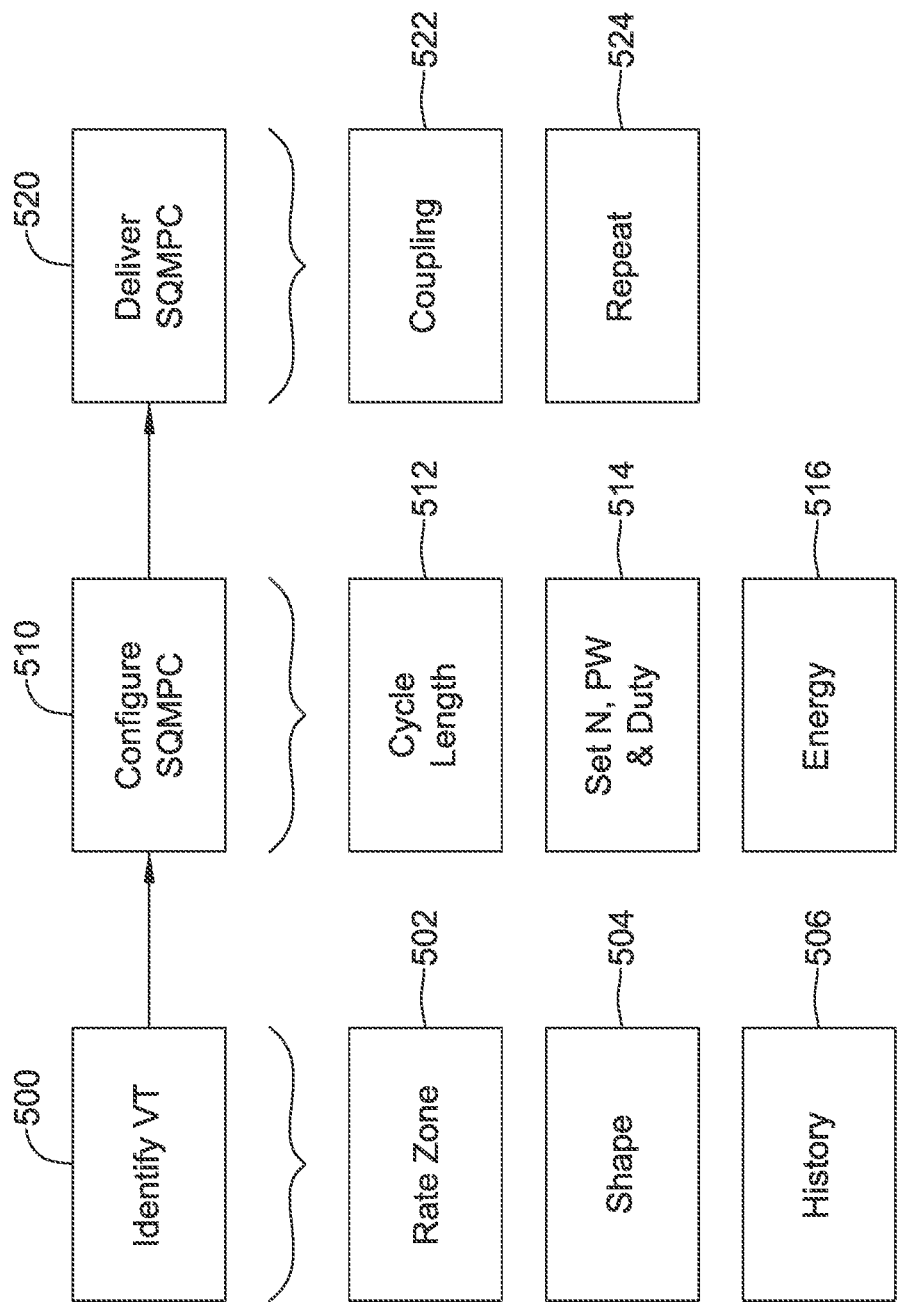
FIG. 11 is a block flow diagram for a subcutaneous multiple pulse cardioversion therapy.

FIG. 11 is a block flow diagram for a subcutaneous multiple pulse cardioversion therapy. At block 500, a ventricular tachycardia is identified. Next, a subcutaneous multiple pulse cardioversion therapy is configured at 510. Finally, the multiple pulse cardioversion therapy is delivered at 520.

The steps relating to identifying the ventricular tachycardia 500 may again include consideration of the rate 502 and shape, morphology or width 504, and patient history 506. Configuring the subcutaneous multiple pulse cardioversion at 510 again includes an identification of cycle length 512.

The therapy is configured by setting N, the number of pulses, as well as the pulse width and duty cycle to be used, as noted at 514. In this example, the multiple pulse cardioversion will comprise a plurality of at least 2, and up to 10, or more, individual pulses delivered within the time period of a single cycle length of the VT 512. As indicated at 516, how energetic the therapy is can be set, for example by selecting an overall energy, or a pulse amplitude in terms of current or voltage, or by selecting an actual energy target, or by other steps. While this example is directed toward delivery of the pulses within a single cycle length of the VT 512, in other examples, an overall duration may be selected using a multiple or fraction of the cycle length, or using a fixed period that may be extended or shortened in light of prior failure or success, for example.

In some examples, the individual pulse widths in the multi-pulse therapy are variable, as is the inter-pulse period, to accommodate a selected number of such pulses within a given period of time which may be the cycle length of the VT 512. In an alternative example, the individual pulses of the multi-pulse therapy may be delivered at a fixed frequency in the range of 10 to 100 Hertz, for example, with either variable or fixed pulse widths.

In some embodiments noted below with reference to FIG. 13, a single device or system may be configured to make several different therapies available such as subcutaneous ATP, subcutaneous low energy cardioversion, subcutaneous multiple pulse cardioversion, and subcutaneous defibrillation. In some such examples, among the lower power/energy therapies, the subcutaneous multiple pulse cardioversion may be preferred over subcutaneous ATP and subcutaneous low energy conversion, with the subcutaneous ATP preferred over subcutaneous low energy conversion. Other examples may apply different preferences.

Delivery of the subcutaneous multiple pulse therapy is performed at 520. Unlike some of the other examples herein, therapy delivery does not need to be synchronized, necessarily, though it may be if desired. A coupling interval is set at 522, though this step may be considered optional. In one example, however, the coupling interval 522 is set as a percentage (less than 100%) of the calculated cycle length, to define a delay after the last detected R-wave or QRS complex.

If a first therapy delivery fails to terminate the ventricular tachycardia, therapy may be repeated at 524. One or more therapy delivery parameters may be changed before repeating. For example, the amplitude or energy 516 may be increased. Duty cycle, pulse width, or the number of individual pulses 514 may be changed as well. In one example, the total energy 516 remains approximately the same, but the number of individual pulses delivered within the single cycle length is increased. Such a change may occur by decreasing pulse width while adding to the number of pulses, for example. Alternatively, the number of pulses may be increased or decreased while also increasing the output energy.

Figure 12:
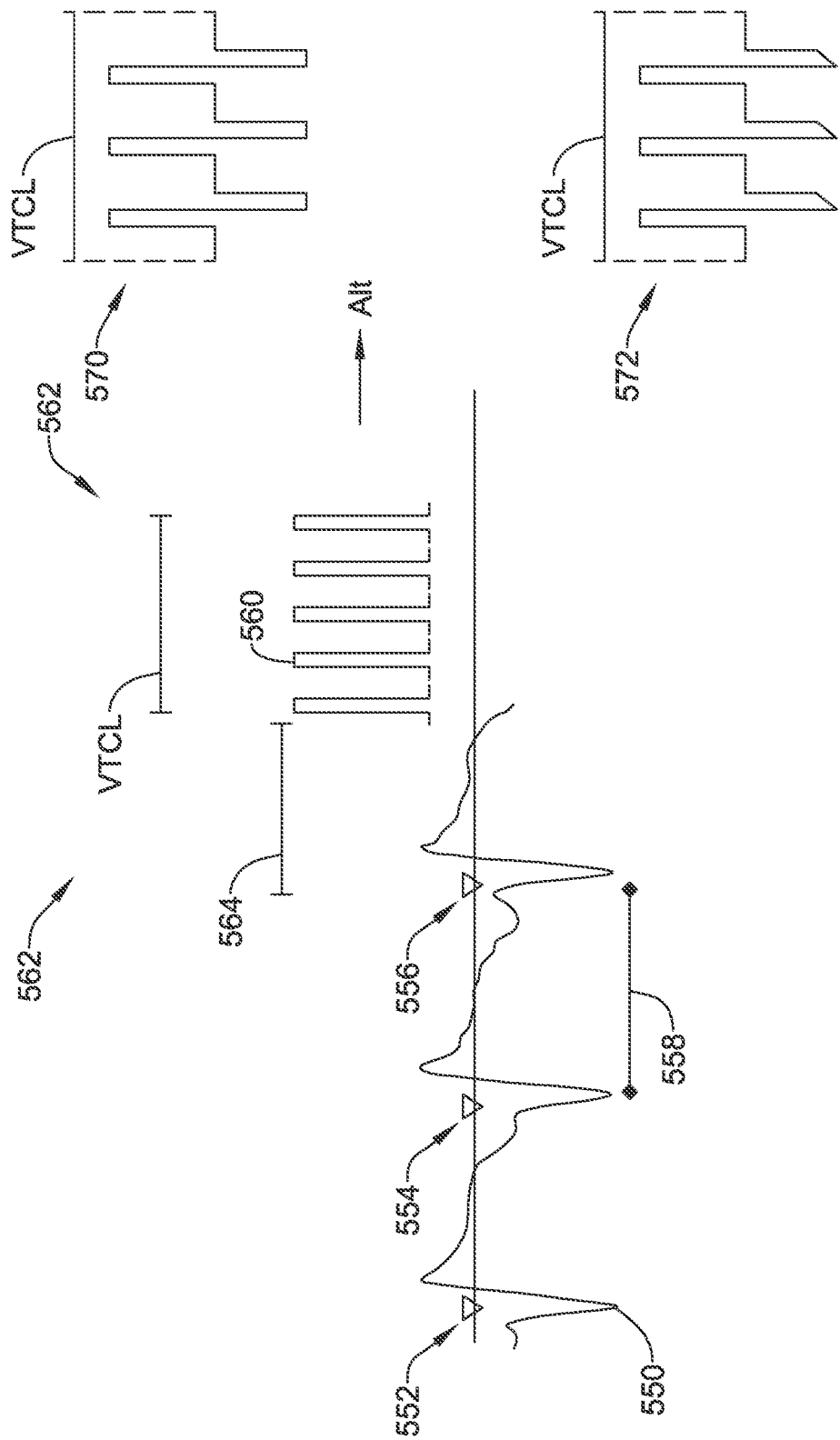
FIG. 12 is a graphic illustration of the delivery of a subcutaneous multiple pulse cardioversion therapy.

FIG. 12 is a graphic illustration of the delivery of a subcutaneous multiple pulse cardioversion therapy. The subcutaneous ECG is shown at 550, and R-wave detections are noted at 552, 554, and 556. An average cycle length is calculated, as indicated at 558. Next, a plurality of individual pulses 560 are delivered in a time period that is less than the average ventricular tachycardia cycle length, as shown at 562. Optionally, therapy delivery may be provided after expiration of a coupling interval shown at 564; the coupling interval 564 may be fixed or predefined, or may be a percentage (less than 100%) of the average cycle length 558.

A set of monophasic and constant amplitude pulses are shown at 560. These may be constant voltage or constant current pulses, if desired. Alternatively, a number of biphasic pulses may be delivered as shown at 570. In another alternative, the individual pulses may be ramped, decaying, etc., as shown at 572.

In the example of FIGS. 11-12, the therapy occurs within a period equal to the average ventricular cycle length. In other examples, a different maximum period may be permitted.

In one alternative example, the "history" assessments made in FIGS. 2, 9 and 11 while identifying a ventricular tachycardia may be specifically tailored for a system having each of the different therapy types available. For example, a single device may comprise the circuitry and stored, machine readable instruction sets to deliver each of a subcutaneous anti-tachycardia pacing therapy, a subcutaneous low energy cardioversion therapy, and a subcutaneous multiple pulse cardioversion therapy. When considering the patient history in any of FIGS. 2, 9 and 11, a determination may be made as to whether an identified ventricular tachycardia matches characteristics of a previously treated ventricular tachycardia. FIG. 13 is illustrative.

Figure 13:
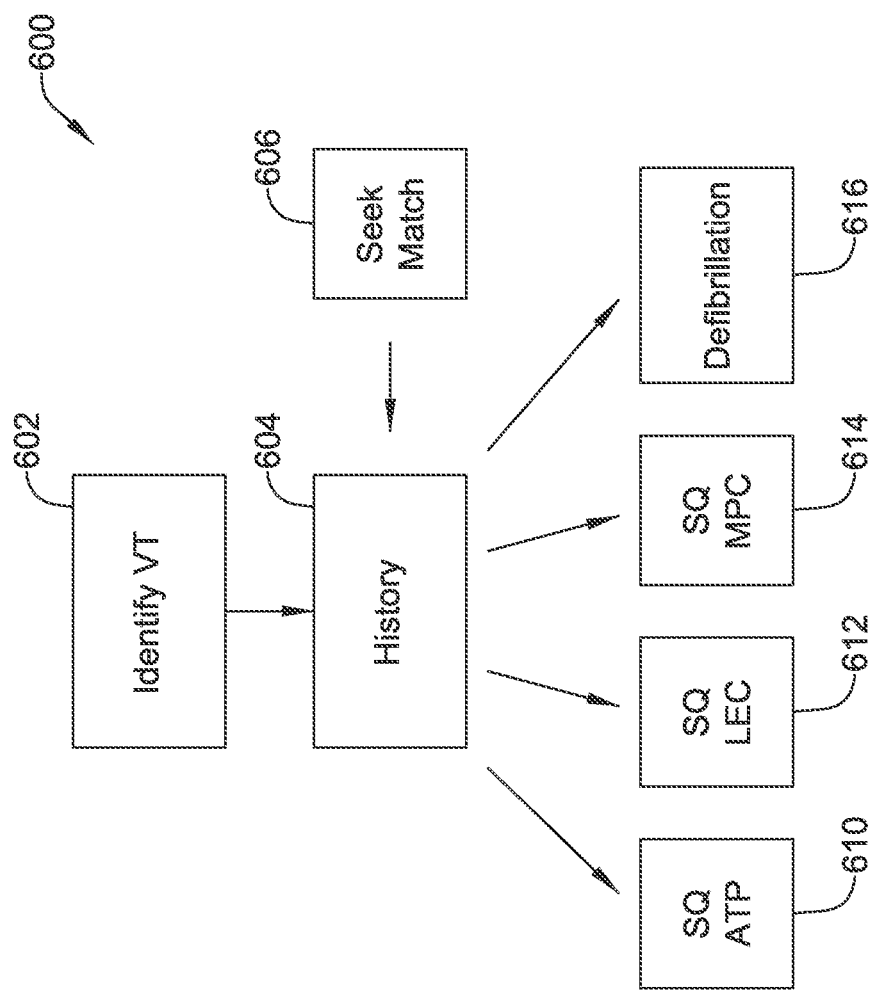
FIG. 13 illustrates, in block form, a method of selecting among therapies.

FIG. 13 is a block flow diagram for a set of choices that may be made using patient history. As shown at 600, once a ventricular tachycardia is identified at 602, the patient history is assessed. One or more stored characteristics of a previously treated ventricular tachycardias may be compared to the characteristics of the identified ventricular tachycardia to seek a match, as noted at 606. If there is a match, a decision regarding which of the available therapies to use can be made. For example, if a matching previous ventricular tachycardia was successfully converted with one of a subcutaneous ATP therapy 610, a subcutaneous low energy cardioversion therapy 612, or a subcutaneous multiple pulse cardioversion therapy 614, then the same therapy can be selected again. In another example, if one of therapies 610, 612 or 614 was previously attempted and failed, then a re-attempt with the same therapy, but different parameters (higher energy, different coupling, ramp instead of burst, more "N", etc.) may be applied. In another example, if one of the therapies 610, 612, 614 was previously applied to an arrhythmia matching the identified ventricular tachycardia and failed, then that therapy would not be re-tried. In another example, if a therapy 610, 612, 614 was previously applied to a matching arrhythmia, and the previous attempt caused an apparent acceleration, then the system may withhold all therapy until sufficient data is captured to justify going directly to a defibrillation therapy 616.

For a new device or a device lacking therapy history, block 604 may select which therapy 610, 612, 614 or even 616 to try first by reference to one or more physician preferences, or by reference to features of the identified ventricular tachycardia. In one example, the multiple pulse cardioversion therapy 614 is attempted first for a given patient for a given VT episode and, if failed, either a parameter of the multiple pulse cardioversion therapy 614 is modified (i.e., high amplitude or energy, more pulses, or other changes), or a different therapy may be applied. For another example, multiple therapy tiers may be used, for example, a lower rate ventricular tachycardia may be treated with subcutaneous ATP 610 first, while a higher rate ventricular tachycardia receives a subcutaneous multiple pulse cardioversion therapy 614 first, and a very high rate polymorphic ventricular tachycardia advances directly to defibrillation 616. In one example, within block 604, there may be determination of whether there has been a prior (successful) ambulatory therapy delivery, with matches 606 only sought for ambulatory events, to distinguish in-clinic therapy from ambulatory therapy. Alternatively, any prior therapy, whether in or out of the clinic, may be assessed in block 604.

If a VT fails to convert, but remains a VT, in response to delivered non-defibrillation therapy, other non-defibrillation therapies may be tried. If a VT accelerates to a polymorphic arrhythmia or fibrillation, then the high power defibrillation therapy 616 may then be applied.

Block 604 may include more than checking device history. For example, block 604 may include analyzing the detected VT to ensure it is not in need of defibrillation 616 and is instead suitable for one of the other therapy modes 610, 612, 614. For example, such a determination may check that the observed cardiac rate of the identified VT is below a ventricular fibrillation (VF) threshold, which ordinarily would be set by the physician for a given implantable device. The VT threshold would typically be in the range of 180 to 250 beats per minute. In addition, to rule out a need for defibrillation, the identified VT may be assessed to determine whether it is polymorphic, for example, and if it is not polymorphic, then the VT may be considered suitable for treatment by one or more of the therapy modes at 610, 612, 614.

In some examples, a tiering of therapy choices may be set based on a combination of perceived patient discomfort and energy usage. For example, defibrillation 616 may be a last resort since it will be felt as a major shock to the patient and uses the most energy, typically having one or more energy parameters (voltage, current and/or delivered energy) that is an order of magnitude larger than the other therapies 610, 612, 614. The subcutaneous lower energy cardioversion 612 and subcutaneous multiple-pulse cardioversion 614 may be the next preferred tiers, with subcutaneous ATP 610 least preferred insofar as each pulse of the ATP 610 may be felt by the patient as a separate therapy, while the set of closely spaced pulses within a subcutaneous multiple pulse conversion may be felt as a single output. Finally, the subcutaneous multiple pulse cardioversion 614 may use less energy, than the subcutaneous low energy cardioversion 612 (depending on selected parameters), making 614 the most preferred of the three lower energy choices 610, 612, 614.

Other examples may set the tiers differently. For example, the actual VT signal 602 may be assessed to determine how likely or unlikely it is to provide good synchronization information. Since blocks 610 and 612 are more affected by synchronization than block 614, if the ECG appears likely to provide poor synchronization data, then the subcutaneous multiple pulse cardioversion 614 may be most preferred; alternatively, with good synchronization available, the low energy cardioversion 612 may be selected instead. One way to determine if there is likely to be good synchronization information would be to look at one or more of template matching scores, which if high suggest a reasonably repeatable signal that may provide good fiducial points. Another way to make such a determination would be by reference to a second signal indicative of the R-wave and comparing to the time at which detection threshold crossings occur or a time identified using other R-wave identifiers noted above in FIG. 5. Yet another way to make such a determination would be to calculate a signal-to-noise ratio for the cardiac signal by comparing the peak within the refractory period after a detection threshold crossing to the average signal across the cardiac cycle or a maximum non-refractory peak.

VARIOUS NOTES & EXAMPLES

A first non-limiting example takes the form of a method of terminating an arrhythmia by delivery of therapy from a subcutaneous implantable device comprising: identifying a ventricular tachycardia occurring in the heart of a patient; configuring an anti-tachycardia pacing therapy for the patient; delivering the configured anti-tachycardia pacing therapy to the patient using first and second electrodes both disposed subcutaneously in the patient; wherein: the anti-tachycardia pacing therapy comprises at least a first therapy pulse and one or more additional therapy pulses; the step of configuring the anti-tachycardia pacing therapy comprises identifying a cycle length for the ventricular tachycardia and setting one or more parameters defining a duration between the first therapy pulse and at least one of the one or more additional therapy pulses as a percentage of the cycle length; the step of delivering the configured anti-tachycardia pacing therapy comprises: detecting a cardiac cycle by comparing a subcutaneously-captured cardiac signal to a threshold and declaring a cardiac cycle when the threshold is exceeded by the subcutaneously-captured cardiac signal; identifying a synchronization reference point from the detected cardiac cycle by searching for a peak relative to the point in time when the threshold is exceeded by the subcutaneously-captured cardiac signal; and delivering the first therapy pulse at a point in time set relative to the reference point.

A second non-limiting example takes the form of a method as in the first non-limiting example, wherein each of the therapy pulses of the anti-tachycardia pacing therapy are separated from one another, in time, by an equal interval. A third non-limiting example takes the form of a method as in the first non-limiting example, wherein the one or more additional therapy pulses comprise a second therapy pulse and a third therapy pulse, such that a first interval separates the first therapy pulse from the second therapy pulse, and a second interval separates the second therapy pulse from the third therapy pulse, and the first interval is longer than the second interval. A fourth non-limiting example takes the form of a method as in any of the first to third non-limiting example, wherein the step of delivering the first therapy pulse at a point in time set relative to the reference point is performed by waiting for a first-pace interval to expire, wherein the first-pace interval is set as a percentage of a cycle length of the ventricular tachycardia. A fifth non-limiting example take the form of a method as in any of the first to fourth non-limiting examples, wherein the anti-tachycardia pacing is delivered in a biphasic, constant current waveform.

A sixth non-limiting example takes the form of a method as in any of the first to fifth non-limiting examples, wherein the implantable device is configured to detect cardiac cycles according to a default method of cardiac signal analysis, and wherein the step of detecting a cardiac cycle, when performed as part of the step of delivering the configured anti-tachycardia pacing therapy, does not use the default method of cardiac signal analysis. A seventh non-limiting example takes the form of a method as in the sixth non-limiting example, wherein: the default method of cardiac signal analysis uses a first filtering setting for filtering the subcutaneously-captured cardiac signal; and the step of detecting a cardiac cycle, when performed as part of the step of delivering the configured anti-tachycardia pacing therapy, uses a second filtering setting different from the first filtering setting. An eighth non-limiting example takes the form of a method as in either of the sixth or seventh non-limiting examples, wherein: the default method of cardiac signal analysis compares the subcutaneously captured cardiac signal against a time-varying detection threshold to detect cardiac cycles; and the step of detecting a cardiac cycle, when performed as part of the step of delivering the configured anti-tachycardia pacing therapy, comprises comparing the subcutaneously captured cardiac signal against a flat detection threshold to detect cardiac cycles.

A ninth non-limiting example takes the form of a method of terminating an arrhythmia by delivery of therapy from a subcutaneous implantable device comprising: identifying a ventricular tachycardia occurring in the heart of a patient; and delivering a low energy cardioversion therapy to the patient using first and second electrodes both disposed subcutaneously in the patient; wherein: the low energy cardioversion therapy comprises a single therapy pulse; the step of delivering the low energy cardioversion therapy comprises: detecting a cardiac cycle by comparing a subcutaneously-captured cardiac signal to a threshold and declaring a cardiac cycle when the threshold is exceeded by the subcutaneously-captured cardiac signal; identifying a synchronization reference point from the detected cardiac cycle by searching for a peak relative to the point in time when the threshold is exceeded by the subcutaneously-captured cardiac signal; and delivering the low energy cardioversion therapy at a point in time set relative to the reference point.

A tenth non-limiting example takes the form of a method as in the ninth non-limiting example, wherein the step of delivering the low energy cardioversion therapy at a point in time set relative to the reference point is performed by waiting for a coupling interval to expire, wherein the coupling interval is set as a percentage of a cycle length of the ventricular tachycardia. An eleventh non-limiting example takes the form of a method as in either of the ninth or tenth non-limiting examples, wherein the low energy cardioversion therapy is delivered in a biphasic, constant current waveform.

A twelfth non-limiting example takes the form of a method as in any of the ninth to eleventh non-limiting examples, wherein the implantable device is configured to detect cardiac cycles according to a default method of cardiac signal analysis, and wherein the step of detecting a cardiac cycle, when performed as part of the step of delivering the low energy cardioversion therapy, does not use the default method of cardiac signal analysis. A thirteenth non-limiting example takes the form of a method as in the twelfth non-limiting example, wherein: the default method of cardiac signal analysis uses a first filtering setting for filtering the subcutaneously-captured cardiac signal; and the step of detecting a cardiac cycle, when performed as part of the step of delivering the low energy cardioversion therapy, uses a second filtering setting different from the first filtering setting. A fourteenth non-limiting example takes the form of a method as in either of the twelfth or thirteen non-limiting examples, wherein: the default method of cardiac signal analysis compares the subcutaneously captured cardiac signal against a time-varying detection threshold to detect cardiac cycles; and the step of detecting a cardiac cycle, when performed as part of the step of delivering the low energy cardioversion therapy, comprises comparing the subcutaneously captured cardiac signal against a flat detection threshold to detect cardiac cycles.

A fifteenth non-limiting example takes the form of a method of terminating an arrhythmia by delivery of therapy from a subcutaneous implantable device comprising: identifying a ventricular tachycardia occurring in the heart of a patient; calculating a cycle length of the ventricular tachycardia; delivering a multiple pulse cardioversion therapy to the patient using first and second electrodes both disposed subcutaneously in the patient; wherein: the multiple pulse cardioversion therapy comprises at least first and second therapy pulses delivered during an interval that is equal to or less than the cycle length of the tachycardia.

A sixteenth non-limiting example takes the form of a metho as in the fifteenth non-limiting example, wherein the step of delivering the multiple pulse cardioversion therapy comprises: detecting a cardiac cycle by comparing a subcutaneously-captured cardiac signal to a threshold and declaring a cardiac cycle when the threshold is exceeded by the subcutaneously-captured cardiac signal; identifying a synchronization reference point from the detected cardiac cycle by searching for a peak relative to the point in time when the threshold is exceeded by the subcutaneously-captured cardiac signal; and delivering the multiple pulse cardioversion therapy at a point in time set relative to the reference point. A seventeenth non-limiting example takes the form of a method as in the sixteenth non-limiting example, wherein the step of delivering the multiple pulse cardioversion therapy at a point in time set relative to the reference point is performed by waiting for a coupling interval to expire, wherein the coupling interval is set as a percentage of a cycle length of the ventricular tachycardia.

An eighteenth non-limiting example takes the form of a method as in either of the sixteenth or seventeenth non-limiting examples, wherein the implantable device is configured to detect cardiac cycles according to a default method of cardiac signal analysis, and wherein the step of detecting a cardiac cycle, when performed as part of the step of delivering the multiple pulse cardioversion therapy, does not use the default method of cardiac signal analysis. A nineteenth non-limiting example takes the form of a method as in the eighteenth non-limiting example, wherein: the default method of cardiac signal analysis uses a first filtering setting for filtering the subcutaneously-captured cardiac signal; and the step of detecting a cardiac cycle, when performed as part of the step of delivering the multiple pulse cardioversion therapy, uses a second filtering setting different from the first filtering setting. A twentieth non-limiting example takes the form of a method as in either of the eighteenth to nineteenth non-limiting examples, wherein: the default method of cardiac signal analysis compares the subcutaneously captured cardiac signal against a time-varying detection threshold to detect cardiac cycles; and the step of detecting a cardiac cycle, when performed as part of the step of delivering the multiple pulse cardioversion therapy, comprises comparing the subcutaneously captured cardiac signal against a flat detection threshold to detect cardiac cycles.

A twenty-first non-limiting example takes the form of a method as in any of the fifteenth to twentieth non-limiting examples wherein the multiple pulse cardioversion therapy comprises a series of monophasic, constant current waveforms separated by equal intervals. A twenty-second non-limiting example takes the form of a method as in any of the first to twenty-first non-limiting examples, wherein all electrodes and components of the subcutaneous implantable device are disposed between the ribs and skin of the patient.

A twenty-third non-limiting example takes the form of an implantable cardiac stimulus system comprising: an implantable device comprising a housing containing operational circuitry for analyzing cardiac signals and providing therapy outputs, the implantable device configured to couple to an implantable lead; and an implantable lead having one or more electrodes thereon for implantation subcutaneously in a patient, the implantable lead being compatible with the implantable device; wherein the operational circuitry is configured to perform a method as in any of the first to twenty-first non-limiting examples.

A twenty-fourth non-limiting example takes the form of an implantable cardiac stimulus system comprising: an implantable device comprising a housing containing operational circuitry for analyzing cardiac signals and providing therapy outputs, the implantable device configured to couple to an implantable lead; and an implantable lead having one or more electrodes thereon for implantation subcutaneously in a patient, the implantable lead being compatible with the implantable device; wherein the operational circuitry is configured to select from among at least first, second and third therapy modes for treating a ventricular tachycardia by doing the following: observing characteristics of a sensed ventricular tachycardia (VT) to ensure it is not requiring the first therapy mode; determining that a current VT is not requiring the first therapy mode, and: comparing characteristics of the current VT to stored data from prior therapy delivery of at least one of the second and third therapy modes and determining whether there is a match to a VT previously treated successfully with one of the second and third therapy modes; if it is determined that there is a match, delivering therapy according to whichever of the second and third therapy modes has previously treated successfully a VT that is a match to the current VT; and if it is determined that there is no match, delivering therapy according to the second therapy mode.

A twenty-fifth non-limiting example takes the form of a system as in the twenty-fourth non-limiting example, wherein the first therapy mode is defibrillation, the second therapy mode is a subcutaneous multiple pulse cardioversion therapy, and the third therapy is a subcutaneous anti-tachycardia pacing therapy.

A twenty-sixth non-limiting example takes the form of an implantable cardiac stimulus system comprising: an implantable device comprising a housing containing operational circuitry for analyzing cardiac signals and providing therapy outputs, the implantable device configured to couple to an implantable lead; and an implantable lead having one or more electrodes thereon for implantation subcutaneously in a patient, the implantable lead being compatible with the implantable device; wherein the operational circuitry is configured to select from among at least first, second and third therapy modes, the first the first therapy mode being a defibrillation therapy mode, and the second and third therapy modes at least an order of magnitude less energy than the first therapy mode, for treating a ventricular tachycardia, by doing the following: determining that a current VT is suitable for therapy by one of the second and third therapy modes; comparing characteristics of the current VT to stored data from prior therapy delivery of at least one of the second and third therapy modes and determining whether there is a match to a VT previously treated successfully with one of the second and third therapy modes; if it is determined that there is a match, delivering therapy according to whichever of the second and third therapy modes has previously treated successfully a VT that is a match to the current VT; and if it is determined that there is no match, delivering therapy according to the second therapy mode.

A twenty-seventh non-limiting example takes the form of an implantable cardiac stimulus system comprising: an implantable device comprising a housing containing operational circuitry for analyzing cardiac signals and providing therapy outputs, the implantable device configured to couple to an implantable lead; and an implantable lead having one or more electrodes thereon for implantation subcutaneously in a patient, the implantable lead being compatible with the implantable device; wherein the operational circuitry is configured to select from among at least first, second and third therapy modes, the first the first therapy mode being a defibrillation therapy mode, and the second and third therapy modes at least an order of magnitude less energy than the first therapy mode, for treating a ventricular tachycardia, by doing the following: determining that a current VT is suitable for therapy by one of the second and third therapy modes; determining whether a prior VT has been treated by the implantable device and, if so, comparing characteristics of the current VT to stored data from prior therapy delivery of at least one of the second and third therapy modes and determining whether there is a match to a VT previously treated successfully with one of the second and third therapy modes; if it is determined that there is a match, delivering therapy according to whichever of the second and third therapy modes has previously treated successfully a VT that is a match to the current VT; and if no prior VT has been treated by the implantable device, or if there is no match, delivering therapy according to the second therapy mode.

A twenty-eighth non-limiting example takes the form of an implantable cardiac stimulus system comprising: an implantable device comprising a housing containing operational circuitry for analyzing cardiac signals and providing therapy outputs, the implantable device configured to couple to an implantable lead; and an implantable lead having one or more electrodes thereon for implantation subcutaneously in a patient, the implantable lead being compatible with the implantable device; wherein the operational circuitry is configured to select from among at least first and second therapy modes for treatment of an identified ventricular tachycardia (VT) by: observing one or more characteristics of a cardiac signal containing the identified VT to determine whether synchronization is likely to be accurate and: if it is determined that synchronization is likely to be accurate, selecting the first therapy mode; or if it is not determined that synchronization is likely to be accurate, selecting the second therapy mode; and wherein, once the VT is identified and the first or second therapy mode is selected, the operational circuitry is configured to deliver a therapy to the patient using the selected first or second therapy mode.

It should be noted in reference to any of these non-limiting examples in which synchronization is an element that each of the examples of synchronization data sources discussed in relation to FIG. 5 may be used alone or in combination. It should also be noted that any reference to a constant voltage or constant current, or an exponential decay, ramp or other output waveform shape, may be only so exact as the hardware of a given system may support. For example, a "constant current" source will have some intrinsic ripple and/or error (some small percentage or absolute error), and may shift depending on the load into which it is applied, as well as having outer boundaries (the current cannot remain constant as the load goes to infinity).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of terminating an arrhythmia by delivery of therapy from an implantable medical device comprising:
    identifying a ventricular tachycardia occurring in the heart of a patient;
    configuring an anti-tachycardia pacing therapy for the patient;
    delivering the configured anti-tachycardia pacing therapy to the patient using first and second electrodes both disposed in the patient without entering or touching the heart; wherein:
    the anti-tachycardia pacing therapy comprises at least a first therapy pulse and one or more additional therapy pulses;
    the step of configuring the anti-tachycardia pacing therapy comprises setting a first pace interval to be used for determining when to deliver the first therapy pulse, and identifying a cycle length for the ventricular tachycardia and setting one or more parameters defining a duration between the first therapy pulse and at least one of the one or more additional therapy pulses as a percentage of the cycle length;
    the step of delivering the configured anti-tachycardia pacing therapy comprises:
        detecting a cardiac cycle by comparing a captured cardiac signal to a threshold and declaring a cardiac cycle when the threshold is exceeded by the captured cardiac signal, the cardiac signal having been captured using electrodes implanted without entering or touching the heart;
        identifying a synchronization reference point from the detected cardiac cycle by searching for a peak relative to the point in time when the threshold is exceeded by the captured cardiac signal; and
        delivering the first therapy pulse at a point in time set relative to the synchronization reference point by waiting for the first-pace interval to expire after the synchronization reference point; and
    the first-pace interval is set as a percentage of a cycle length of the ventricular tachycardia.

2. The method of claim 1 wherein each of the therapy pulses of the anti-tachycardia pacing therapy are separated from one another, in time, by an equal interval.

3. The method of claim 1 wherein the one or more additional therapy pulses comprise a second therapy pulse and a third therapy pulse, such that a first interval separates the first therapy pulse from the second therapy pulse, and a second interval separates the second therapy pulse from the third therapy pulse, and the first interval is longer than the second interval.

4. A method as in claim 1 wherein the implantable device is configured to detect cardiac cycles according to a default method of cardiac signal analysis, and wherein the step of detecting a cardiac cycle, when performed as part of the step of delivering the configured anti-tachycardia pacing therapy, does not use the default method of cardiac signal analysis.

5. A method as in claim 4 wherein the default method of cardiac signal analysis uses a first filtering setting for filtering the captured cardiac signal, and the step of detecting a cardiac cycle, when performed as part of the step of delivering the configured anti-tachycardia pacing therapy, uses a second filtering setting different from the first filtering setting, and wherein the first filtering setting is applied to the captured cardiac signal to flatten out the baseline and second, modified filtering settings are applied to the cardiac signal to promote synchronization.

6. A method as in claim 4, wherein the default method of cardiac signal analysis compares the captured cardiac signal against a time-varying detection threshold to detect cardiac cycles, and the step of detecting a cardiac cycle, when performed as part of the step of delivering the configured anti-tachycardia pacing therapy, comprises comparing the captured cardiac signal against a flat detection threshold to detect cardiac cycles.

7. A method as in claim 1 wherein the first and one or more additional therapy pulses take the form of biphasic, constant current therapy pulses.

8. A method as in claim 1 wherein the implantable medical device is a subcutaneous only defibrillator comprising an implantable pulse generator and a lead each of which is implanted subcutaneously in the patient, such that the step of delivering the first therapy pulse is performed using first and second subcutaneously implanted electrodes.

9. A method as in claim 1 wherein the implantable medical device is an extravascular defibrillator comprising an implantable pulse generator and a substernal lead having a portion that resides beneath the sternum without entering or touching the heart, such that the step of delivering the first therapy pulse uses an electrode on the pulse generator and an electrode on the substernal lead.

10. A method as in claim 1 wherein the implantable medical device is an extravascular defibrillator comprising an implantable pulse generator and a substernal lead having a portion that resides beneath the sternum without entering or touching the heart, such that the step of delivering the first therapy pulse uses first and second electrodes disposed on the substernal lead.

11. An implantable cardiac stimulus system comprising:
an implantable device comprising a housing containing operational circuitry for analyzing cardiac signals and providing therapy outputs; and
an implantable lead having one or more electrodes thereon for implantation in a patient without entering or touching the heart, the implantable lead adapted to couple the electrodes to the operational circuitry of the implantable device;
wherein the operational circuitry is configured to:
identify a ventricular tachycardia occurring in the heart of a patient by analysis of cardiac signals captured using one or more of the electrodes on the implantable lead;
configure an anti-tachycardia pacing therapy for the patient;
deliver the configured anti-tachycardia pacing therapy to the patient using at least one electrode of the lead;
wherein:
the operational circuitry is adapted such that the anti-tachycardia pacing therapy comprises at least a first therapy pulse and one or more additional therapy pulses;
the operational circuitry is adapted to configure the anti-tachycardia pacing therapy by setting a first pace interval to be used for determining when to deliver the first therapy pulse, and identifying a cycle length for the ventricular tachycardia and setting one or more parameters defining a duration between the first therapy pulse and at least one of the one or more additional therapy pulses as a percentage of the cycle length;
the operational circuitry is adapted to deliver the configured anti-tachycardia pacing therapy by:
detecting a cardiac cycle by comparing a captured cardiac signal to a threshold and declaring a cardiac cycle when the threshold is exceeded by the captured cardiac signal, the cardiac signal having been captured using electrodes implanted without entering or touching the heart;
identifying a synchronization reference point from the detected cardiac cycle by searching for a peak relative to the point in time when the threshold is exceeded by the captured cardiac signal; and
delivering the first therapy pulse at a point in time set relative to the synchronization reference point by waiting for the first-pace interval to expire after the synchronization reference point, and
the first-pace interval is a percentage of a cycle length of the ventricular tachycardia.

12. The system of claim 11 wherein the operational circuitry is configured such that each of the therapy pulses of the anti-tachycardia pacing therapy are separated from one another, in time, by an equal interval.

13. The system of claim 11 wherein the operational circuitry is configured such that the one or more additional therapy pulses comprise a second therapy pulse and a third therapy pulse, such that a first interval separates the first therapy pulse from the second therapy pulse, and a second interval separates the second therapy pulse from the third therapy pulse, and the first interval is longer than the second interval.

14. The system of claim 11 wherein the operational circuitry is configured to detect cardiac cycles according to a default method of cardiac signal analysis that uses a first filtering setting for filtering the captured cardiac signal, and to use a second filtering setting different from the first filtering setting to detect a cardiac cycle in order to deliver the configured anti-tachycardia pacing therapy, and wherein the first filtering setting is applied to the captured cardiac signal to flatten out the baseline and second, modified filtering settings are applied to the cardiac signal to promote synchronization.

15. The system of claim 11 wherein the operational circuitry is configured to detect cardiac cycles according to a default method of cardiac signal analysis by comparing the captured cardiac signal against a time-varying detection threshold to detect cardiac cycles, and is further configured to detect a cardiac cycle in order to deliver the configured anti-tachycardia pacing therapy by comparing the captured cardiac signal against a flat detection threshold.

16. The system of claim 11 wherein the operational circuitry is configured such that the first and one or more additional therapy pulses take the form of biphasic, constant current therapy pulses.

17. The system of claim 11 wherein the lead is adapted for subcutaneous-only placement without touching or entering the heart.

18. The system of claim 11 wherein the lead is adapted for placement in a substernal location without touching or entering the heart.

* * * * *